Figures 1, 2:
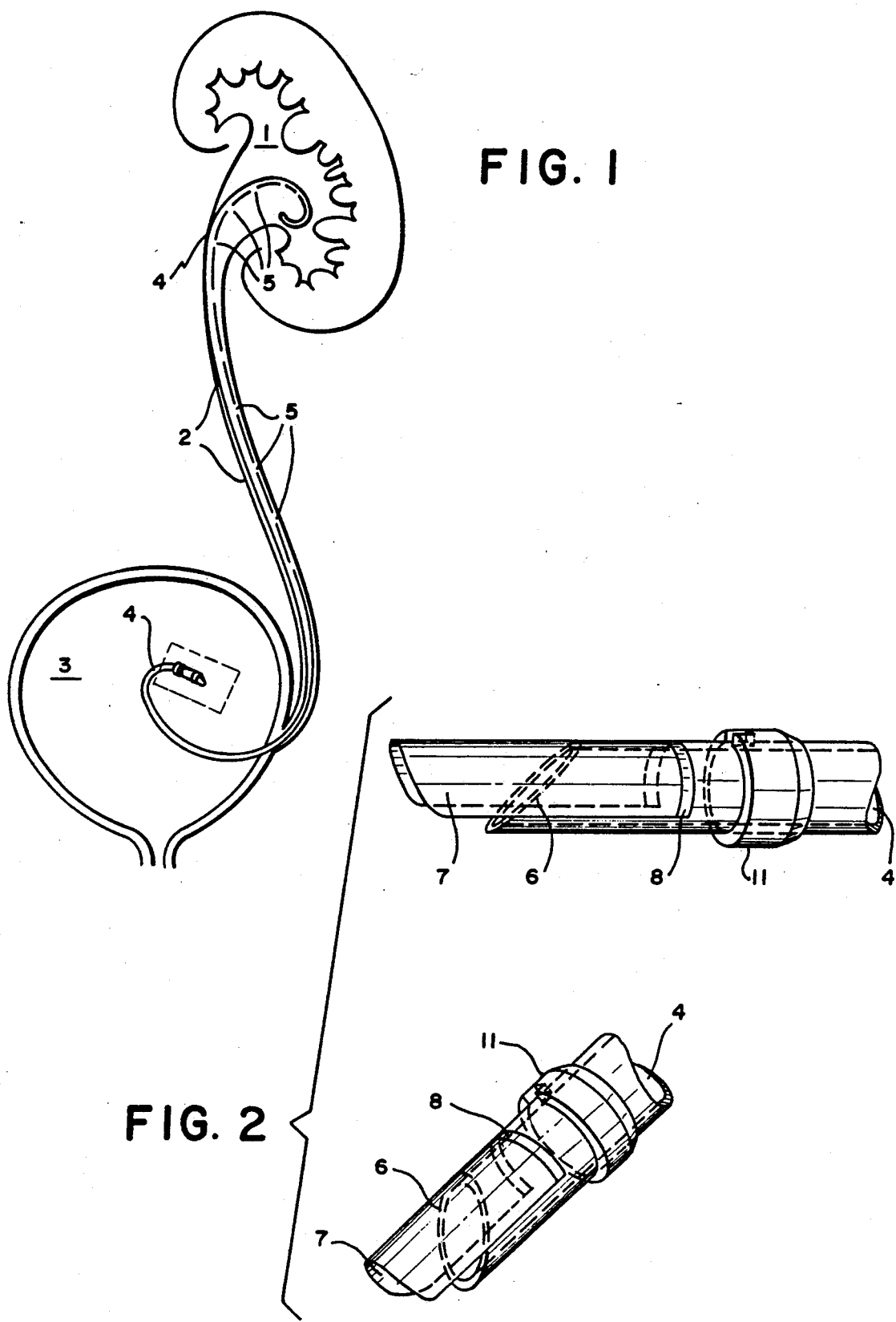

United States Patent [19]

Hoene

[11] Patent Number: 5,019,102

[45] Date of Patent: May 28, 1991

[54] ANTI-REFLUXIVE INTERNAL URETERAL STENT WITH A DYNAMIC HOOD-VALVE AT THE VESICAL END FOR PREVENTION OF URINARY REFLUX INTO THE UPPER URINARY TRACT UPON INCREASE OF VESICAL PRESSURE

[76] Inventor: Eberhard Hoene, Warburghof 16, D-3000, Hannover 61, Fed. Rep. of Germany

[21] Appl. No.: 382,651

[22] PCT Filed: Dec. 7, 1988

[86] PCT No.: PCT/EP88/01113

§ 371 Date: Aug. 10, 1989

§ 102(e) Date: Aug. 10, 1989

[87] PCT Pub. No.: WO89/05127

PCT Pub. Date: Jun. 15, 1989

[30] Foreign Application Priority Data

Dec. 10, 1987 [DE] Fed. Rep. of Germany ....... 3741832

[51] Int. Cl.$^5$ .............................................. A61F 2/04
[52] U.S. Cl. ........................................ 623/12; 623/2; 623/11; 604/323; 604/264; 604/281
[58] Field of Search ................... 623/1, 2, 11, 12, 900; 604/264, 280, 281, 323

[56] References Cited

U.S. PATENT DOCUMENTS

| | | |
|---|---|---|
| 3,965,900 | 6/1976 | Boedecker ............................. 604/323 |
| 3,999,551 | 12/1976 | Spitz et al. . |
| 4,334,327 | 6/1982 | Lyman et al. . |
| 4,512,770 | 4/1985 | Cianci et al. . |
| 4,574,806 | 3/1986 | McCarthy . |
| 4,643,732 | 2/1987 | Pietsch et al. ........................ 623/2 |
| 4,671,795 | 6/1987 | Mulchin ............................... 604/281 |
| 4,685,905 | 8/1987 | Jeanneret nee Aab . |
| 4,759,758 | 7/1988 | Gabboy ............................... 623/900 |

FOREIGN PATENT DOCUMENTS

| | | |
|---|---|---|
| 0208841 | 10/1986 | European Pat. Off. . |
| 1250704 | 9/1960 | Fed. Rep. of Germany . |
| 3339179 | 10/1983 | Fed. Rep. of Germany . |
| 86-14013.2 | 5/1986 | Fed. Rep. of Germany . |
| 2133083 | 4/1971 | France . |
| 2409747 | 11/1977 | France . |
| 2611486 | 9/1988 | France ................................. 623/12 |
| WO/8001507 | 7/1980 | Int'l Pat. Institute . |

Primary Examiner—Randall L. Green
Assistant Examiner—Paul Prebilic
Attorney, Agent, or Firm—Shlesinger, Arkwright & Garvey

[57] ABSTRACT

An anti-refluxive internal ureteral stent includes a ureteral catheter which is closed at its renal end and is provided with lateral perforations only in the upper and middle portions thereof. The stent includes a hood-valve at it vesical end to prevent urinary reflux. The hood-valve comprises a hood-shaped plastic foil that partially surrounds the external circumferential surface of the catheter at the oblique vesical end opening. The hood-valve is open in its resting state so as to allow the urine to flow out through the vesical outlet, unimpeded by the hood-valve, and folds over to close the vesical outlet in response to a reflux pressure generated due to a pressure differential between the catheter and the bladder. The valve remains closed until the pressure differential subsides. The urine flows into the catheter via multiple lateral openings in the upper and middle portions thereof. A gelatin cap generally enclosing the valve may be slipped over the vesical end of the catheter to serve as a stop for the guide-wire during insertion of the stent in a patient. The gelatin cap is pushed off by the guide-wire into the bladder where is it dissolved in the urine. This arrangement permits insertion of the catheter from above without damaging hood-valve during surgical procedures.

17 Claims, 4 Drawing Sheets

ANTI-REFLUXIVE INTERNAL URETERAL STENT WITH A DYNAMIC HOOD-VALVE AT THE VESICAL END FOR PREVENTION OF URINARY REFLUX INTO THE UPPER URINARY TRACT UPON INCREASE OF VESICAL PRESSURE

The invention concerns an anti-refluxive internal ureteral stent in accordance with the preceding patent claims.

Internal ureteral stents are customarily used to conduct urine out of the pelvic-calceal system into the bladder when normal urine transport is compromised by constriction of the ureter, for instance by scar formation, external encroachment of congenital stricture or by obstruction of the ureteral lumen, for instance by urinary calculus, clot or tumor.

The purpose of such stents is to guard against the threat of damage to the renal parenchyme from persistently high pressure, and to prevent life-threatening infection of the "stagnant waters" in the upper urinary tract.

Internal ureteral stents in present use are tube-shaped, synthetic catheters with curvature at both ends, the radius of the upper coil, above the uretero-pelvic junction, being smaller than that of the lower coil in the bladder, in order to block dislocation in either direction. The stents carry numerous lateral (punched) perforations, particularly in the portions to be positioned in the renal pelvis and the bladder, guaranteeing inflow and outflow during lengthy indwelling periods, and in case of incrustation of single openings. In order check positioning, the synthetic catheters give X-ray contrast, by using radio-opaque material either for the entire tube or for a longitudinal skein in the wall of the tube.

The insertion of customary ureteral stents is occasioned by threading in a much longer and considerably stiffer guide-wire to straighten the forementioned curvatures. Retrograde insertion of the stent catheters is carried out through the working port of a cystoscope under visual and fluoroscopic guidance, threading them into the lower ureteral outlet—the ostium—and advancing them up the ureter with the help of the guide-wire. A second synthetic tube is threaded onto the guide-wire, reaching from the end of the ureteral catheter almost to the end of the guide-wire, thus leaving the latter free for manipulation. When the internal ureteral catheter is correctly placed, the free end of the second synthetic tube is fixed by hand and the guide-wire is drawn out through its lumen. During this extraction, the vesical end of the stent is braced against the synthetic tube, so that friction in the coiled portions does not extract the stent catheter from the ureter along with the guide-wire. This procedure is carried out under visual cystoscopic guidance; as soon as the guide-wire lies only in the outer synthetic tube—the stop-tube—the vesical end of the stent is freed and coils up in the bladder as dictated by the vesical curvature.

Safeguarding urinary outflow to the bladder to date with customary internal catheter stents is bought at the expense of periodically recurrent, unphysiological pressure peaks in the upper urinary tract. The unimpeded patency of such stents abolishes the anatomical valve function of the lower ureteral orifice, or ostium, which normally protects against urinary reflux. This leads to continuous transmission of any pressure increases in the bladder lumen into the pelvio-calyceal system by reversed urine flow, or reflux. As a result, the patients provided with such stents frequently suffer severe pain. On the one hand, the transmission of the sudden pressure rise during micturition activates stretch receptors in the renal pelvic wall, whose irritation is perceived as pain similar to colics. On the other hand, the presence of foreign bodies in the bladder—and the vesical portion of such stent catheters is a foreign body—frequently leads to painful bladder cramps by irritation of the bladder wall. The pressure waves of these cramps are then perceived as flank pain on the side with an indwelling stent catheter. These patients often are simultaneously treated for obstructive micturition disorders by transurethral catheterization, presenting an access port for germs, which then may unimpedely ascend, with the infected urine, along the internal ureteral catheter, occasionally causing life-threatening infection of the upper unitary tract and renal parenchyme.

Anti-refluxive valves that are closed in their resting state will, for instance, excessively obstruct urine outflow by virtue of their stiffness or, being more pliable, will pose the threat of kinking against the bladder wall, which would lock them closed. Valve forms mounted within the catheter lumen also present an additional impediment to flow, or will have forfeited their capability to close or open after a short time, due to incrustation caused by distal turbulence.

The purpose of the invention under consideration here is to fashion an internal ureteral stent of the type mentioned at the outset, so as to replace the openings in the vesical portion of the catheter by a single, terminal, dynamic valve against reflux. The design of this invention is so conceived as to obviate the various disadvantages of previous concepts.

In contrast to earlier valves, which for various reasons have never reached the stage of clinical trials, the valve presented here is distinguished by:

a) a fully open resting state as continuation of the complete cross section of the catheter;

b) virtually inertialess closure, due to a hydrodynamic principle, upon inception of urinary reflux, when the pressure in the bladder exceeds that in the ureter and pelvic-calyceal system;

c) the impossibility of obstruction from the outside by deformation or kinking;

d) considerable deformation during closure and opening, which frees it of deposits and incrustations, guaranteeing its function even for longer indwelling periods.

Hereinafter, the invention is explained in the light of the enclosed illustrations.

Figure 3A:
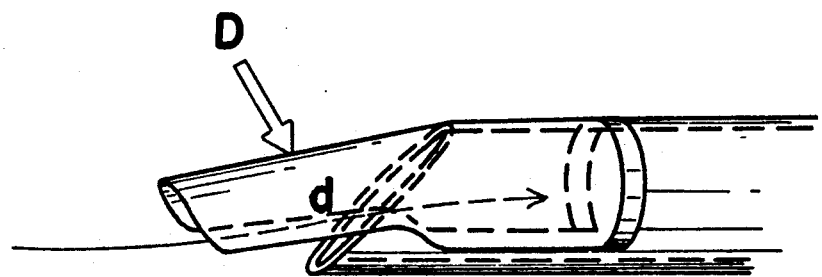
Figure 3B:
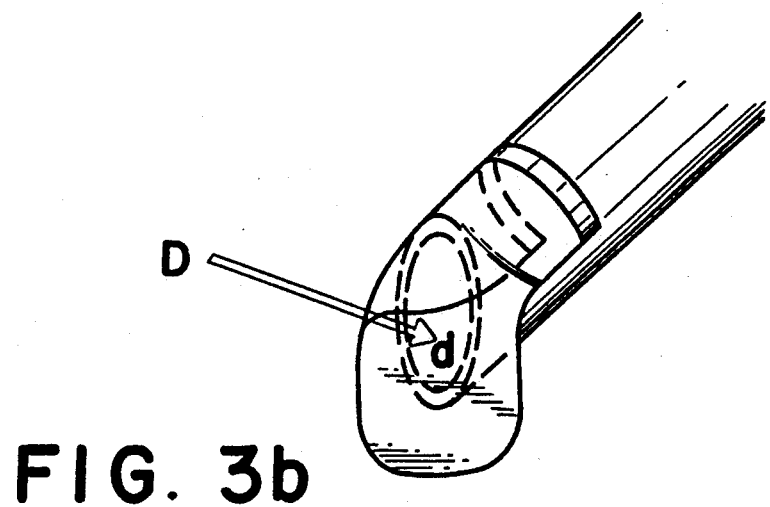
Figures 4A, 4B:
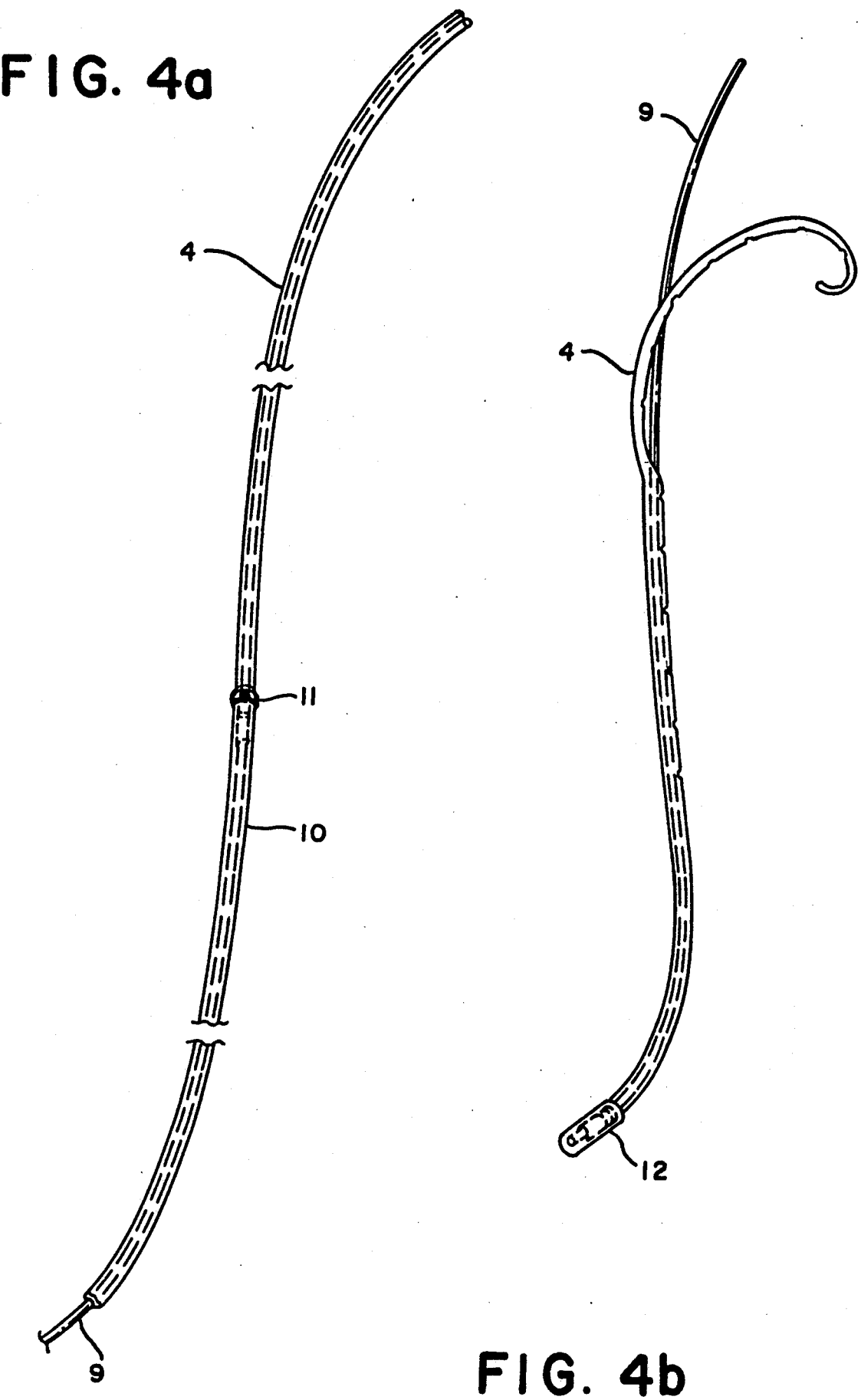
Figure 5:
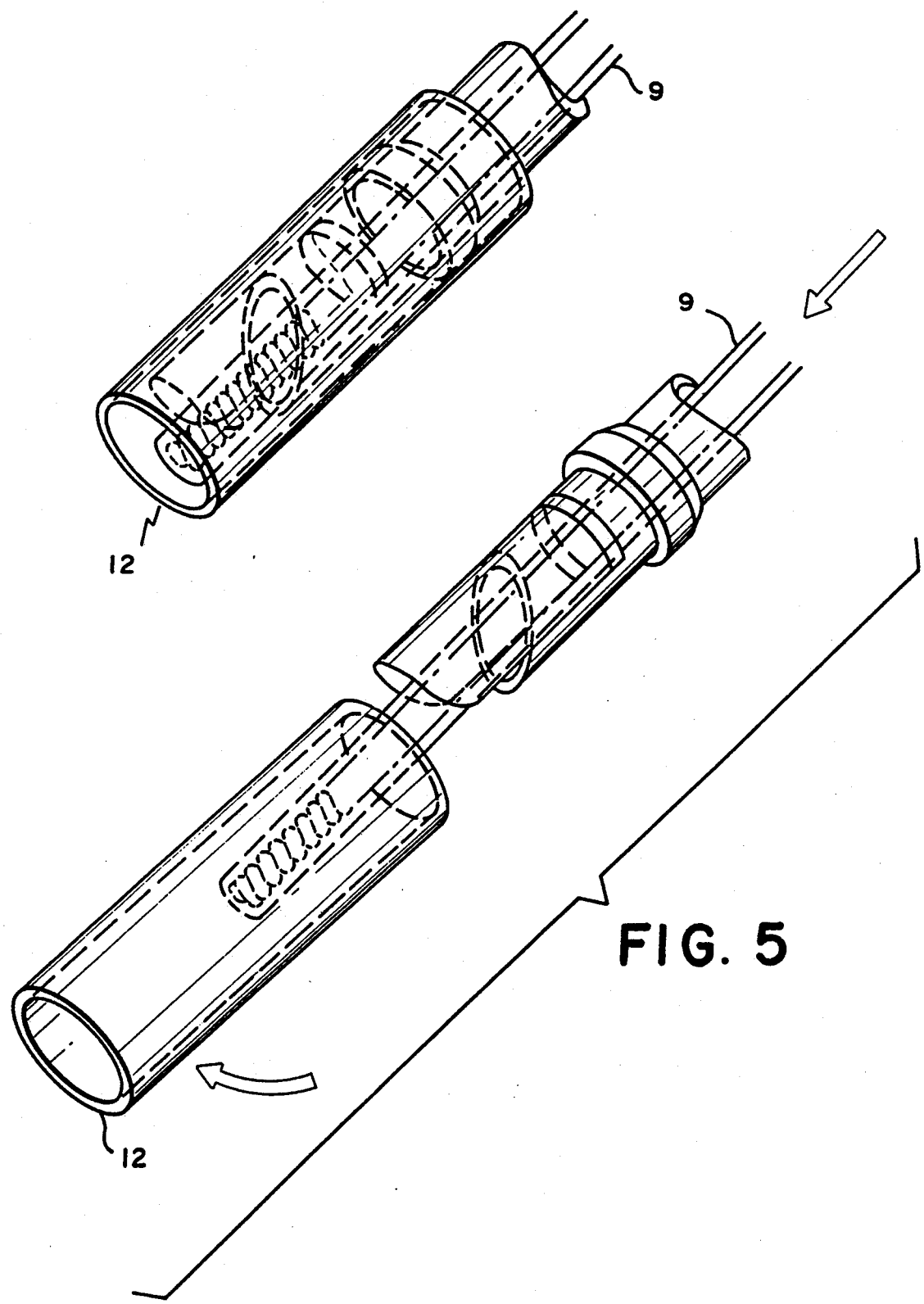
Figure 5:
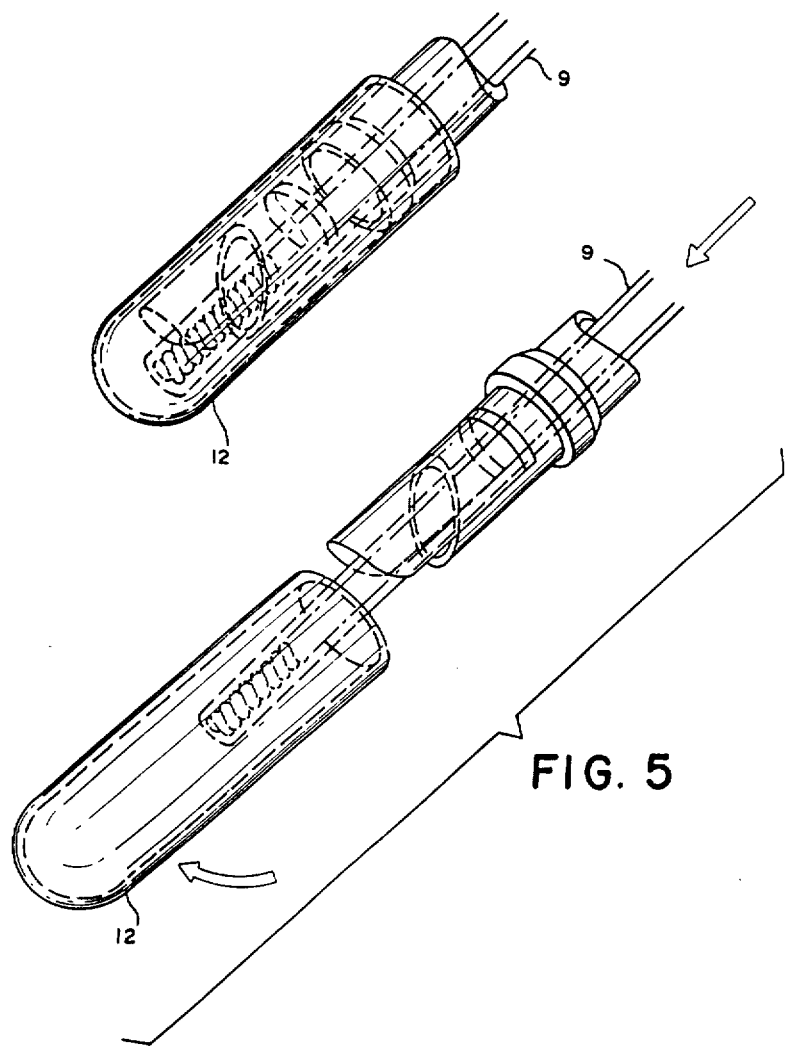

These show:

FIG. 1 in a schematic plan view the correct position of an anti-refluxive, internal ureteral catheter from the pelvic-calyceal system to the bladder;

FIG. 2 as a partial enlargement the vesical end of the catheter stent with the anti-refluxive hood-valve;

FIG. 3 as a further partial enlargement the deformation of the cited valve upon inception of reflux, as well as in the closed state;

FIG. 4 as a schematic representation the insertion of the anti-refluxive internal ureteral catheter with the aid of a guide-wire;

FIG. 5 as a partial enlargement the protective cap for antegrade insertion, as well as its removal, when the anti-reflexive internal ureteral catheter is correctly positioned.

In accordance with this invention, the anti-refluxive, internal ureteral catheter 4 carries lateral perforations 5 only in its upper and middle portions, i.e. in the pelviccalyceal system 1 and in the course of the ureter 2. The lower portion, which comes to lie in the bladder 3, has no lateral perforations; only the vertical end 6, with an oblique outlet facing into the catheter's curvature, is fully open in the resting state of the valve. At a distance sufficing for the deformation required for closure, the foil of the hood-valve 7 is affixed circumferentially 8 to the catheter surface.

The hood-valve 7 is an approximately rectangular sheet of synthetic foil having a generally C-shaped cross-section. The width is approximately twice, the length approximately three times the outer diameter of the ureteral catheter to be fitted with the valve. At one edge of the width, a narrow strip 8 (¼ to ⅓ catheter diameter) is assigned for affixation of the foil to the surface of the internal ureteral catheter. The opposite corners of the sheet are rounded. When affixed to the catheter's circumference, so as to face the terminal obliquity, approximately one catheter diameter from the outlet, the foil encompasses the outer catheter circumference, acquiring the described form as an hoodvalve 7, which extends approximately one catheter diameter past the vesical catheter outlet. The obliquity is inclined so that it faces the hood valve 7.

Valve closure results from the hyprodynamic principle named after Venturi (FIGS. 3a and b). When the bladder pressure increases, incipient urinary reflux occasions retrograde flow through the valve, leading to a reduction of pressure here in comparison to the pressure in the rest of the bladder. The pressure gradient between ambient bladder pressure (D) and that within the valve (d) takes with it the light hood of foil, flattening it and deforming it laterally, to lay it upon the terminal catheter outlet, closing the latter until the outside pressure increment subsides, for instance at the end of micturition. The elasticity of the foil hood then forces it back into the resting form, thus freeing the terminal outlet of the stent. The repetitive deformation during closure and opening leads to early disruption and dispersal of developing incrustation.

The thickness of the foil must suffice to resist the pressure difference in the closed state, preventing inversion of the foil into the closed catheter outlet. The inherent degree of rigidity then guarantees its return to the curvature of the catheter circumference to which the valve is affixed, assuring that the valve maintains the fully open form of its resting state. On the other hand, the foil must be sufficiently light and flexible to follow even a slight pressure gradient, being flattened and deformed in the process, to occlude the oblique, terminal catheter outlet.

The foil hood does not encompass the entire circumference of the catheter, but leaves the portion of circumference on the opposite side of the obliquity—about ⅓ of the entire circumference—uncovered. In other words, the foil hood surrounds about two-thirds the external circumferential surface of the catheter. Even when displaced slightly to one side or the other, a partial sheath of this design suffices to securely occlude the catheter outlet, and is furthermore easier to deform and flatten during closure. In addition, the wide open gap gives protection against undesired impediment to outflow, for instance by kinking or distortion of the hoodvalve against the bladder wall.

For transurethral insertion of the anti-refluxive, internal ureteral catheter through a cystoscope, advancing it up the ureter into the pelvic-calyceal system, the catheter stent is straightened by threading a guide-wire 9 into its lumen up to the bluntly closed renal end. When the internal ureteral stent is positioned correctly, the guidewire is extracted. To prevent simultaneous withdrawal of the stent, a second syntehtic tube is employed in customary systems, reaching from the vesical end of the stent to just short of the end of the guide-wire. This second tube, subsequently designated as the stop-tube 10, is fixed by hand outside the cystoscope, while the guide-wire is extracted through its lumen, and prevents concurrent extraction of the ureteral stent, which in previous models is braced against the end of the stoptube. This is unfeasible here, because it could lead to damage of the delicate hood-valve.

In accordance with this invention, the stop-tube 10 is designed with an inner diameter slightly exceeding the outer diameter of the stent with the valve, so that it can accommodate the vesical end of the stent. On the stent itself, a ring-shaped abutment 11, slightly above the hood-valve, or at the level of its edge of fixation 8, serves as an abutment ring for the stop-tube, while the guide-wire is extracted. As soon as the latter lies only in the stop-tube, it may be employed to push the vesical end of the stent out of the stop-tube under visual guidance with the cystoscope.

The abutment ring 11 is fashioned with a rectangular notch at its rim, to accommodate a corresponding projection at the rim of the stop-tube 10. This achieves dirigibility of the ureteral stent during insertion. Torsional rotation at the free end of the stop-tube is then transmitted into corresponding rotation of the ureteral stent 4 with the guide-wire 9, so that the renal end of the stent may be directed in the desired direction.

When the ureteral stent is inserted from above, the invention provides for protection of the hood-valve by a water-soluble gelatine cap 12. This loosely envelops the end of the stent with the valve and fits tightly around the abutment ring, where it is held by friction. When the stent is correctly positioned, the cap is pushed off the abutment ring in the bladder, by advancing the guide-wire a short distance, thus uncovering the valve, and dissolves shortly afterwards.

I claim:

1. An anti-refluxive internal ureteral stent, comprising:
   a) a catheter having an open end;
   b) hood valve means secured to said catheter adjacent said one end and having open and closed positions for opening and closing the opening thereof;
   c) said hood valve means being actuated by a reflux pressure to assume said closed position;
   d) said hood valve means including a flap member having a first free end portion; and
   e) said flap member extending a distance beyond the open end so that when said hood valve means assumes said closed position, said flap member folds over thereby completely covering the open end and said first free end portion thereof extends beyond the perimeter of the open end.

2. The ureteral stent of claim 1, wherein:
   a) said flap member assumes said open position when said reflux pressure subsides.

3. The ureteral stent of claim 1, wherein:
   a) said flap member is generally C-shaped in crosssection.

4. The internal stent of claim 1, wherein:

a) said flap member includes a second end portion affixed to said catheter a distance away from the open end thereof.

5. The ureteral stent of claim 4, wherein:
a) said second end portion of said flap member is affixed to an external circumferential surface of said catheter in a partial surrounding relationship thereto.

6. The ureteral stent of claim 5, wherein:
a) said second end portion of said flap member surrounds about two-thirds of the external circumferential surface of said catheter.

7. The ureteral stent of claim 4, wherein:
a) said distance is about the diameter of said catheter.

8. The ureteral stent of claim 1, wherein:
a) said flap member is made of an elastic material.

9. The ureteral stent of claim 1, wherein:
a) the open end of said catheter is inclined so that it faces said flap member.

10. The ureteral stent of claim 1, further including:
a) straightening means removably insertable in said catheter for proper positioning of the stent in a patient.

11. The ureteral stent of claim 10, further including:
a) stop means for preventing withdrawal of said catheter when said straightening means is removed therefrom.

12. The ureteral stent of claim 11, wherein:
a) said stop means includes a tubular member having an inside diameter larger than the outside diameter of said catheter.

13. The ureteral stent of claim 12, wherein:
a) said catheter includes abutment means for positioning said tubular member thereon.

14. The ureteral stent of claim 13, wherein:
a) said abutment means includes a ring-shaped member with a notch; and
b) said tubular member includes a projection member to be received in said notch for securing said stop means on said catheter;
c) wherein a rotation of said stop means is transmitted into simultaneous rotation of said catheter.

15. The ureteral stent of claim 1, further including:
a) means for protecting said hood-valve means while implanting the stent in a patient.

16. The ureteral stent of claim 15, wherein:
a) said valve protecting means includes a cap to be removably secured over said open end of said catheter.

17. The ureteral stent of claim 16, wherein:
a) said cap is made of a water-soluble material.

* * * * *

UNITED STATES PATENT AND TRADEMARK OFFICE
CERTIFICATE OF CORRECTION

PATENT NO. : 5,019,102

DATED : May 28, 1991

INVENTOR(S) : Eberhard Hoene

It is certified that error appears in the above-identified patent and that said Letters Patent is hereby corrected as shown below:

IN THE DRAWINGS:

Sheet 4, Figure 5, the bottom of cap 12 should be closed as shown in Figure 5 of substitute sheet 4, enclosed herewith.

Signed and Sealed this

Twenty-fourth Day of November, 1992

Attest:

DOUGLAS B. COMER

Attesting Officer

Acting Commissioner of Patents and Trademarks